United States Patent [19]

Kase

[11] Patent Number: 5,749,368

[45] Date of Patent: May 12, 1998

[54] BREATH AIR FLOW GAUGE

[76] Inventor: John C. Kase, N70 W5860 Bridge Rd., Cedarburg, Wis. 53012

[21] Appl. No.: 278,097

[22] Filed: Jul. 21, 1994

[51] Int. Cl.[6] .................................... A61B 5/087
[52] U.S. Cl. .................................... 128/725; 482/13
[58] Field of Search .................. 128/716, 725; 84/465, 470; 482/13

[56] References Cited

U.S. PATENT DOCUMENTS

| | | | |
|---|---|---|---|
| 3,451,302 | 6/1969 | Lamon | 84/465 |
| 3,720,202 | 3/1973 | Cleary | 482/13 |
| 3,853,034 | 12/1974 | Vole | 84/465 |
| 4,245,544 | 1/1981 | Hollond | 84/465 |
| 4,533,137 | 8/1985 | Sonne | 128/725 |
| 4,739,987 | 4/1988 | Nicholson | 482/13 |
| 4,973,047 | 11/1990 | Novell | 482/13 |
| 4,981,295 | 1/1991 | Belmon et al. | 128/725 |

*Primary Examiner*—Lee S. Cohen

[57] ABSTRACT

A gauge for measuring the expiratory air flow pressure of an individual. The inventive device includes a main body having an extension tube removably coupled thereto. The extension tube is operable to mount various woodwind or brasswind mouthpieces in fluid communication with the main body. An aperture extends through the main body to permit the exiting of air blown through the device and includes an adjustment means for selectively closing the aperture to simulate air flow through various musical instruments. An air pressure gauge is mounted to the main body in fluid communication therewith to indicate an air flow pressure in both negative and positive directions therewithin. This helps train the respiratory muscles to inhale and exhale the air in a consistent manner which improves tone and breath control.

8 Claims, 3 Drawing Sheets

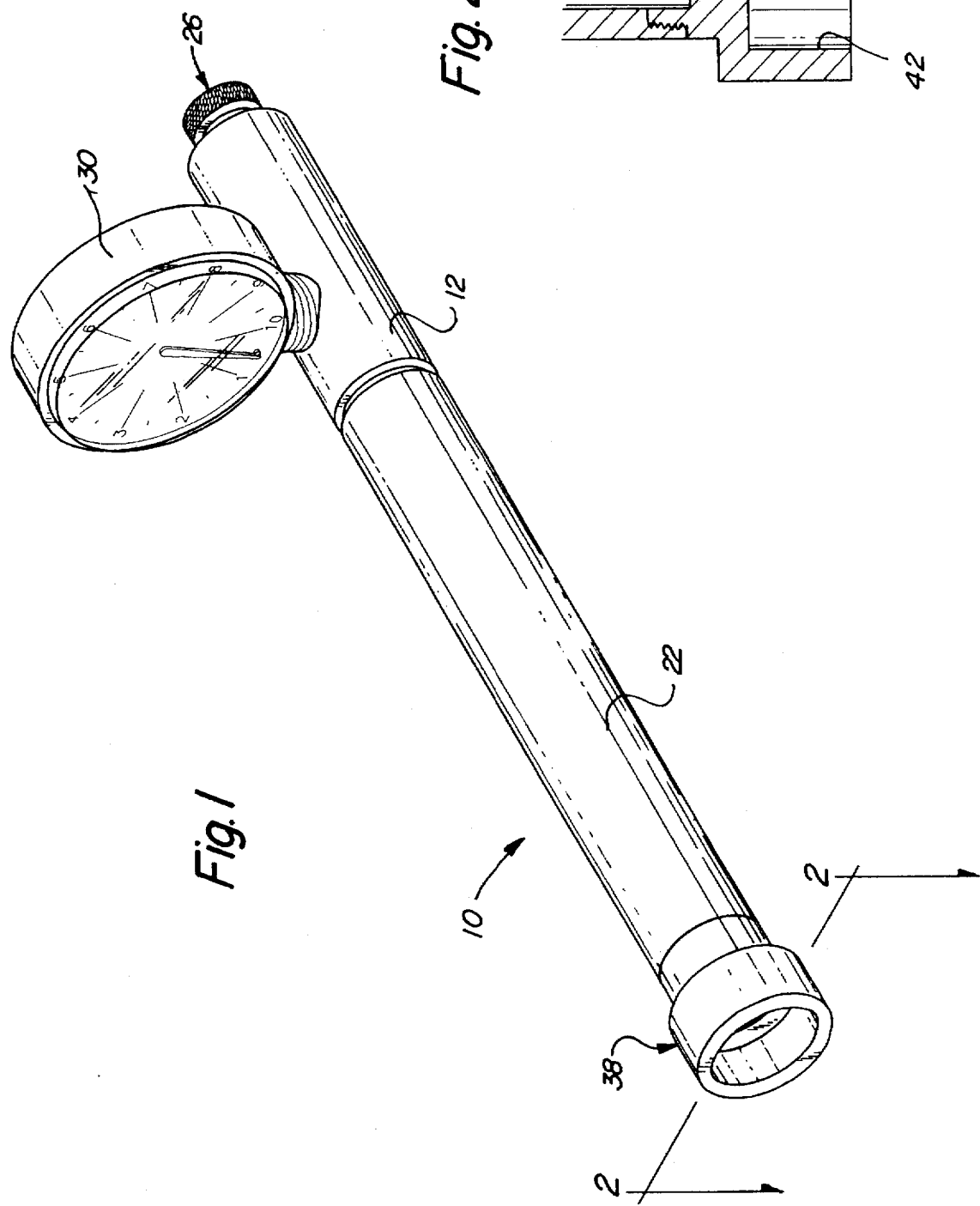

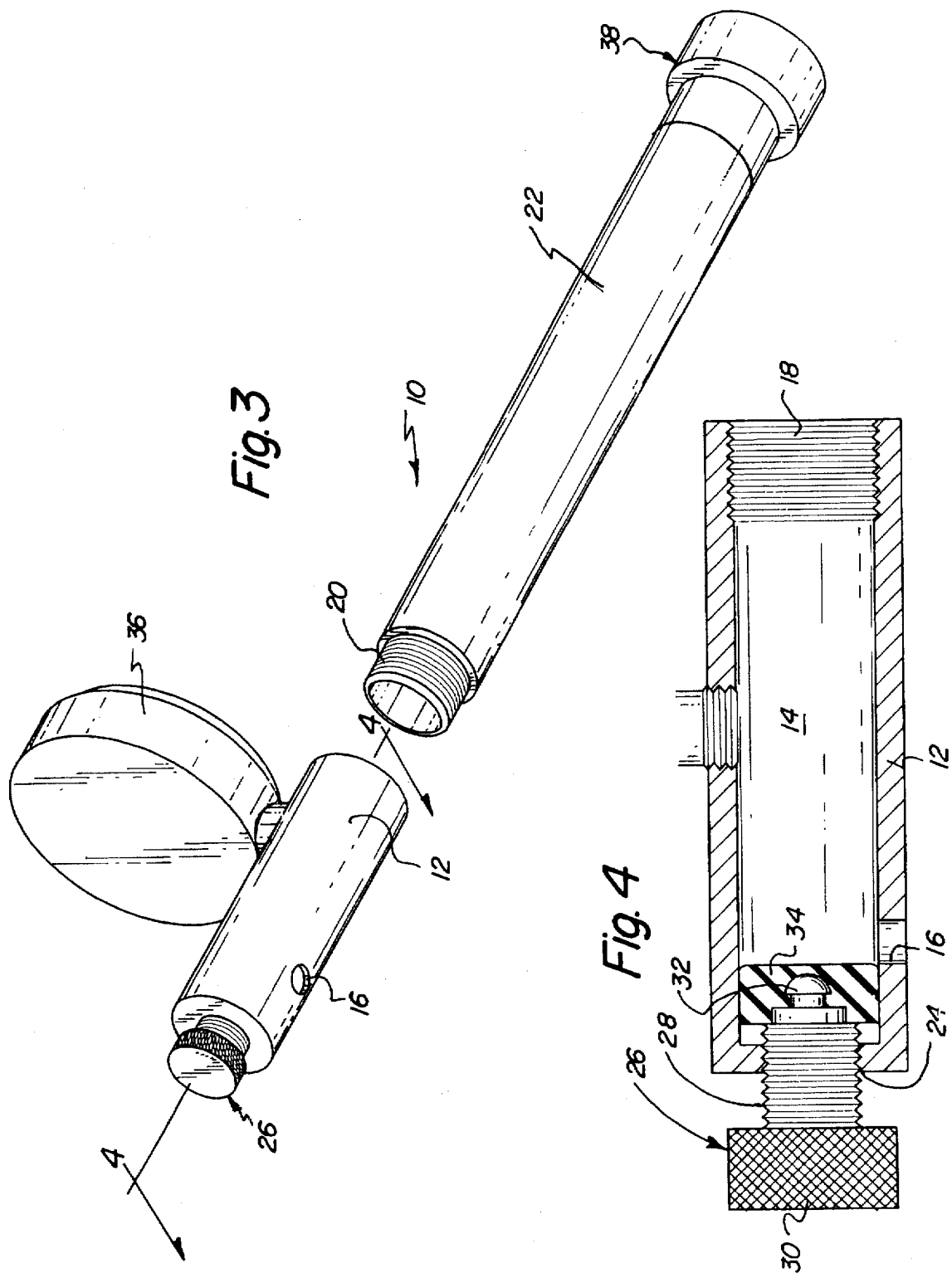

BREATH AIR FLOW GAUGE

BACKGROUND OF THE INVENTION

1. Field of the Invention

The present invention relates to air flow meters and more particularly pertains to a breath air flow gauge for measuring the expiratory air flow pressure of an individual.

2. Description of the Prior Art

The use of air flow meters is known in the prior art. More specifically, air flow meters heretofore devised and utilized for the purpose of measuring air flow expiration from an individual are known to consist basically of familiar, expected and obvious structural configurations, notwithstanding the myriad of designs encompassed by the crowded prior art which have been developed for the fulfillment of countless objectives and requirements.

For example, a spirometer for pulmonary measurement is illustrated in U.S. Pat. No. 4,944,306 which may be utilized to indicate peak flow expiration from a patient, as well as to enhance pulmonary monitoring. The device includes a standard mouthpiece having an orthogonally oriented chamber with a centrally positioned rod guiding a spring biased piston, with the piston being responsive to expiration-induced air flow from the patient.

Another patent of interest is U.S. Pat. No. 4,158,360 which teaches an expiratory flow meter for indicating airway obstruction in a patient. The device includes an elongated channel arranged perpendicularly to a mouthpiece, with an adjustable orifice disposed at one end of the channel. A float moves within the channel in response to expiration from the patient, and a removable pin is provided within the channel for accommodating various ranges of expiration.

Other known prior art air flow meters include U.S. Pat. No. 4,768,520; U.S. Pat. No. 3,695,608; and U.S. Pat. No. 5,234,487.

While these devices fulfill their respective, particular objectives and requirements, the aforementioned patents do not disclose a breath air flow gauge for measuring the expiratory air flow pressure of an individual which includes a main body having an extension tube removably coupled thereto, with the extension tube being operable to mount various woodwind and brasswind mouthpieces in fluid communication with the main body, such that air blown through the device exits through an aperture in the main body, with a pressure gauge indicating air flow pressure within the main body. Furthermore, none of the known prior art air flow meters teach or suggest a breath air flow gauge of the aforementioned structure which further includes an adjustment means for selectively closing the aperture to simulate air flow through various musical instruments.

In these respects, the breath air flow gauge according to the present invention substantially departs from the conventional concepts and designs of the prior art, and in so doing provides an apparatus primarily developed for the purpose of measuring the expiratory air flow pressure of an individual.

SUMMARY OF THE INVENTION

In view of the foregoing disadvantages inherent in the known types of air flow meters now present in the prior art, the present invention provides a new breath air flow gauge construction wherein the same can be utilized for measuring the expiratory air flow pressure of an individual. As such, the general purpose of the present invention, which will be described subsequently in greater detail, is to provide a new breath air flow gauge apparatus and method which has many of the advantages of the air flow meters mentioned heretofore and many novel features that result in a breath air flow gauge which is not anticipated, rendered obvious, suggested, or even implied by any of the prior art air flow meters, either alone or in any combination thereof.

To attain this, the present invention generally comprises a gauge for measuring the expiratory air flow pressure of an individual. The inventive device includes a main body having an extension tube removably coupled thereto. The extension tube is operable to mount various woodwind or brasswind mouthpieces in fluid communication with the main body. An aperture extends through the main body to permit the exiting of air blown through the device and includes an adjustment means for selectively closing the aperture to simulate air flow through various musical instruments. An air pressure gauge is mounted to the main body in fluid communication therewith to indicate an air flow pressure therewithin.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new breath air flow gauge apparatus and method which has many of the advantages of the air flow meters mentioned heretofore and many novel features that result in a breath air flow gauge which is not anticipated, rendered obvious, suggested, or even implied by any of the prior art air flow meters, either alone or in any combination thereof.

It is another object of the present invention to provide a new breath air flow gauge which may be easily and efficiently manufactured and marketed.

It is a further object of the present invention to provide a new breath air flow gauge which is of a durable and reliable construction.

An even further object of the present invention is to provide a new breath air flow gauge which is susceptible of a low cost of manufacture with regard to both materials and labor, and which accordingly is then susceptible of low prices of sale to the consuming public, thereby making such breath air flow gauges economically available to the buying public.

Still yet another object of the present invention is to provide a new breath air flow gauge which provides in the apparatuses and methods of the prior art some of the advantages thereof, while simultaneously overcoming some of the disadvantages normally associated therewith.

Still another object of the present invention is to provide a new breath air flow gauge for measuring the expiratory air flow pressure of an individual.

Yet another object of the present invention is to provide a new breath air flow gauge which includes a main body having a through-extending aperture and an extension tube removably coupled thereto, with the extension tube being operable to mount various woodwind and brasswind mouthpieces in fluid communication with the main body, and a pressure gauge mounted to the main body for indicating air flow pressure therewithin.

Even still another object of the present invention is to provide a new breath air flow gauge which further includes an adjustment means for selectively closing the aperture to simulate air flow through various musical instruments.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a breath air flow gauge comprising the present invention.

FIG. 2 is a cross sectional view taken along line 2—2 of FIG. 1.

FIG. 3 is a bottom isometric view, partially exploded, of the invention.

FIG. 4 is a cross sectional view taken along line 4—4 of FIG. 3.

DESCRIPTION OF THE PREFERRED EMBODIMENT

Figure 5:
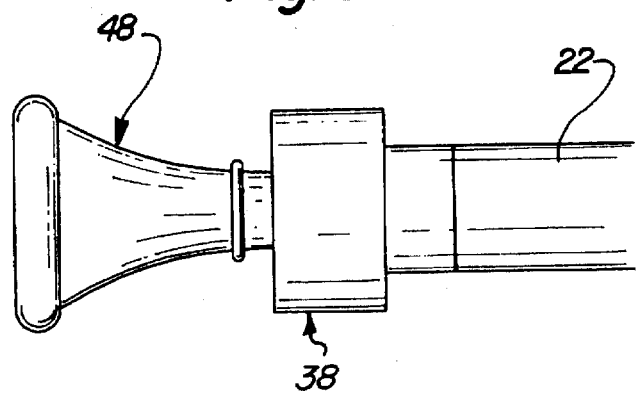
FIG. 5 is a side elevation view of a brasswind mouthpiece comprising a portion of the present invention.

With reference now to the drawings, and in particular to FIGS. 1–6 thereof, a new breath air flow gauge embodying the principles and concepts of the present invention and generally designated by the reference numeral 10 will be described.

More specifically, it will be noted that the breath air flow gauge 10 comprises a main body 12 having a hollow interior 14. The main body 12 is of a substantially circular cross section shape and includes an exit aperture 16 extending through a side wall thereof to permit fluid communication between the hollow interior 14 and the ambient air exterior of the main body 12, as best illustrated in FIGS. 1 and 4. The main body 12 includes a first threaded end 18 for receiving the threaded neck 20 of an elongated extension tube 22, as illustrated in FIG. 3. The extension tube 22 is thereby removably coupled to the main body 12 and may be selectively de-coupled therefrom to facilitate compact storage and transportation of the device 10. The main body 12 further includes a second end 24 through which an adjustment means 26 extends for selectively varying a cross sectional area of the exit aperture 16, thereby regulating a flow of air through the hollow interior 14 of the main body.

As best shown in FIG. 4 of the drawings, the adjustment means 26 comprises a threaded member 28 which threadably extends through an unlabelled threaded aperture in the second end 24 of the main body 12, with the threaded member including a knob 30 which facilitates ease of rotation thereof. The threaded member 28 extends into the hollow interior 14 of the main body 12 and terminates in a projection 32 which rotatably mounts a stopper 34 within the hollow interior. The projection 32 allows the threaded member 28 to rotate relative to the stopper 34, whereby such rotation will axially advance the stopper 34 within the hollow interior 14. Thus, the exit aperture 16 may be selectively opened or closed in an infinitely variable manner.

A rotary pressure gauge 36 is threadably mounted to the main body 12 and extends into fluid communication with the hollow interior 14, as best illustrated in FIG. 4. The rotary pressure gauge 36 is of a conventional design and, therefore, the interior workings of the pressure gauge will not be described in detail. It is important to note, however, that the pressure gauge 36, because of its rotary design, provides an extremely compact design deemed desirable by the present invention 10. Further, and because of its removable, threaded mounting to the main body 12, the pressure gauge 36 may be selectively removed from the main body for compact storage and/or transportation needs. The rotary pressure gauge 36 is operable to indicate air pressure within the interior 14 of the main body 12 relative to ambient exterior air pressure. Indication of air pressure within the main body 12 can be measured by the pressure gauge 36 in both positive and negative directions, thereby facilitating measurement of both the inhaling and exhaling strength, duration, and consistency of the individual utilizing the device 10.

Figure 6:
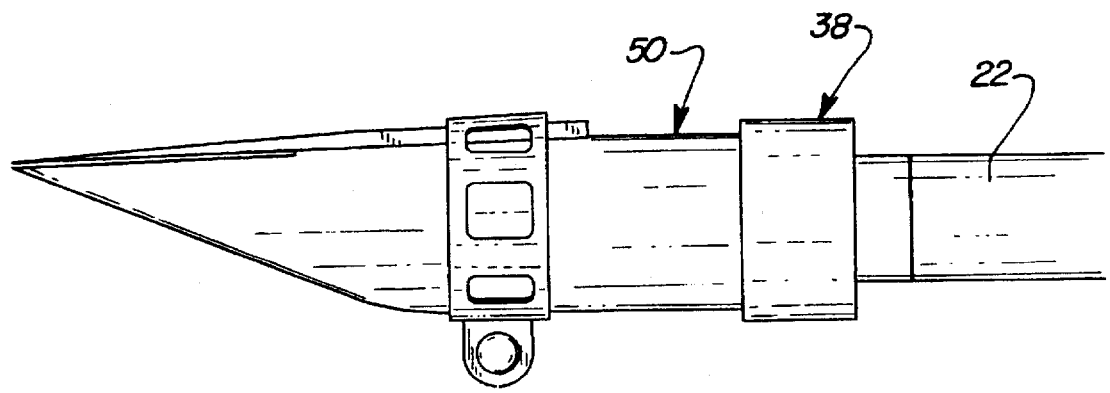
FIG. 6 is a side elevation view of a woodwind mouthpiece comprising a further portion of the present invention.

Referring now to FIGS. 5 and 6, with concurrent reference to FIG. 2, it can be shown that the extension tube 22 includes an adapter 38 having a substantially cylindrical body 40 including a first bore 42 of a first diameter and a second bore 44 of a second diameter. The cylindrical body 40 is removably coupled to the extension tube 22 by a threaded connection 46 which allows for the selective removal of the adapter 38 as desired. The adapter 38 is operable to mount various mouthpieces, such as the brasswind mouthpiece 48 illustrated in FIG. 5, and the woodwind mouthpiece 50 illustrated in FIG. 6. To this end, the first diameter of the first bore 42 is substantially greater than the second diameter of the second bore 44 such that the woodwind mouthpiece 50 may be received within the first bore to removably mount the woodwind mouthpiece to the adapter 38 in fluid communication with the extension tube 22 and hence, the hollow interior 14 of the main body 12. Similarly, the second bore 44 is operable to receive a portion of the brasswind mouthpiece 48 to removably mount the brasswind mouthpiece to the adapter 38 in fluid communication with the extension tube 22 and the hollow interior 14 of the main body 12.

In use, a desired mouthpiece 48, 50 may be attached to the adapter 38, whereby an individual utilizing the device 10 may then blow through the mouthpiece, with the pressure gauge 36 being operable to indicate a pressure within the hollow interior 14 as a result of such expiration relative to the exterior ambient pressure. The adjustment means 26 may then be rotated to restrict the exit aperture 16 to simulate air flow through various musical instruments as desired. Thus, by maintaining the needle of the pressure gauge 36 at a desired numeric value, the individual may practice constant, uniform expiration desirable in the field of musical instruments. Further, the device 10 allows the individual to quantitatively measure the expiration air pressure force generated by the individual. Further, it should be noted that the air flow gauge 10 may be utilized without a mouthpiece 48, 50 by simply utilizing the adapter 38 as a universal mouthpiece.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new breath air flow gauge comprising:

a main body having a hollow interior with an exit aperture extending therethrough;

an elongated extension tube removably coupled to said main body in fluid communication with said interior;

adjustment means for selectively varying a cross sectional area of said exit aperture, thereby regulating a flow of air through said hollow interior of said main body, thereby to simulate air flow through various musical instruments;

a pressure gauge removably mounted to said main body and in fluid communication with said hollow interior for indicating air pressure within said interior of said main body relative to ambient exterior air pressure;

a mouthpiece, and an adapter means removably coupled to said extension tube for facilitating a removable coupling of said mouthpiece to said extension tube in fluid communication with said interior, said adapter means comprises a substantially cylindrical body including a first bore of a first diameter and a second bore of a second diameter, the cylindrical body being removably coupled to said extension tube by a threaded connection, with said first diameter of said first bore being substantially greater than said second diameter of said second bore.

2. The new breath air flow gauge of claim 1, wherein said pressure gauge is operable to measure air pressure within the main body in both positive and negative directions relative to said ambient exterior air pressure.

3. The new breath air flow gauge of claim 1, wherein said mouthpiece comprises a woodwind mouthpiece.

4. The new breath air flow gauge of claim 3, wherein said pressure gauge comprises a rotary pressure gauge.

5. The new breath air flow gauge of claim 4, wherein said pressure gauge is operable to measure air pressure within the main body in both positive and negative directions relative to said ambient exterior air pressure.

6. The new breath air flow gauge of claim 1, wherein said mouthpiece comprises a brasswind mouthpiece.

7. The new breath air flow gauge of claim 6, wherein said pressure gauge comprises a rotary pressure gauge.

8. The new breath air flow gauge of claim 7, wherein said pressure gauge is operable to measure air pressure within the main body in both positive and negative directions relative to said ambient exterior air pressure.

* * * * *